(12) United States Patent
Kobylecki et al.

(10) Patent No.: US 6,664,410 B1
(45) Date of Patent: Dec. 16, 2003

(54) SOLID PHASE NITRILE SYNTHESIS

(75) Inventors: Ryszard Kobylecki, Ely (GB); Neal David Hone, Leamington Spa (GB); Lloyd James Payne, Ely (GB)

(73) Assignee: Millennium Pharmaceuticals Limited (GB)

( * ) Notice: Subject to any disclaimer, the term of this patent is extended or adjusted under 35 U.S.C. 154(b) by 0 days.

(21) Appl. No.: 10/031,221

(22) PCT Filed: Jul. 17, 2000

(86) PCT No.: PCT/GB00/02740

§ 371 (c)(1),
(2), (4) Date: Aug. 13, 2002

(87) PCT Pub. No.: WO01/05747

PCT Pub. Date: Jan. 25, 2001

(30) Foreign Application Priority Data

Jul. 15, 1999  (GB) .............................................. 9916575

(51) Int. Cl.[7] ............................................. C07C 253/00
(52) U.S. Cl. ....................................... 558/309; 558/311
(58) Field of Search .................................. 558/309, 311

(56) References Cited

U.S. PATENT DOCUMENTS 5,767,238 A * 6/1998 Caporale ..................... 530/334
6,392,010 B1 * 5/2002 Salvino et al. .............. 528/486
6,462,076 B2 * 10/2002 Gabriel et al. .............. 514/463

FOREIGN PATENT DOCUMENTS

EP   0 710 645 A1   5/1996

OTHER PUBLICATIONS

Relles et al, "Chemical Transformations with Regenerable, Polmer–Supported Trisubstituted Dlchlorides", CA81:151747, 1974.*

* cited by examiner

Primary Examiner—Deborah C. Lambkin
(74) Attorney, Agent, or Firm—Timothy J. Martin; Michael R. Henson; Rebecca A. Gegick

(57) ABSTRACT

A nitrile compound is prepared by treating a solid supported amide to dehydrate it and cleave it from the support in one operation. The preparation involves acetylation of the amide compound in the presence of a base at a temperature of less than 100° C.

20 Claims, No Drawings

SOLID PHASE NITRILE SYNTHESIS

This invention relates to solid phase nitrile synthesis and particularly, although not exclusively, provides a method of preparing a nitrile compound.

An object of the present invention is to provide an advantageous method of preparing a nitrile compound.

According to the invention, there is provided a method of preparing a nitrile compound, the method comprising treating a solid supported amide to cause formation of the nitrile compound and cleavage from the support.

Thus, there is suitably provided a solid phase reaction which allows formation of nitrites with concomitant release of the solid support. Preferably, in the method, the amide is dehydrated. Preferably the amide is treated such that cleavage and dehydration of the amide are accomplished in one operation.

Said nitrile compound is preferably of formula RCN where R represents an optionally-substituted alicyclic, aliphatic or aromatic (which includes heteroaromatic) group.

Except where otherwise stated in this specification, an alicyclic group may have five or six carbon atoms; it preferably has six. Such a group may be optionally-substituted by any atoms or groups hereinafter described. Additionally, a said alicyclic group may be optionally substituted by forming a polycyclic, for example bicyclic, ring system with other cyclic or aromatic groups. In one embodiment, an alicyclic group may form a bicyclic ring system with a five or six-member aromatic group, an example of this arrangement being a tetrahydronaphthyl group.

Except where otherwise stated in this specification, optional substituents of alicyclic, aliphatic and aromatic groups include halogen atoms for example fluorine, chlorine or bromine atoms and optionally-substituted phenyl, nitro, cyano, alkoxy, hydroxy, amino, alkylamino, sulphinyl, alkylsulphinyl, sulphonyl, amido, alkylamido, alkoxycarbonyl, haloalkyoxycarbonyl and haloalkyl groups. optional substituents, especially nucleophilic groups, also include protected forms of any of the aforesaid.

Except where otherwise stated in this specification, an aliphatic group suitably has up to 8, preferably up to 6, more preferably up to 4, especially up to 2, carbon atoms and may be of straight chain or, where possible, branched chain structure.

Except where other stated in this specification, an aromatic group may include a monocyclic or polycyclic (fused) aromatic ring system. Any aromatic ring of such a system may include one or more heteroatoms selected from nitrogen, oxygen and sulphur atoms. Preferred monocyclic or polycyclic groups include five or six ring atoms.

Where R represents an alicyclic group, it is preferably an optionally-substituted group which includes six ring atoms. Preferably said alicyclic group is substituted so as to define a polycyclic group, especially a bicyclic group, suitably wherein one ring thereof is aromatic. An especially preferred alicyclic group is an optionally-substituted, preferably unsubstituted, tetrahydronaphthyl group.

Where R represents an aliphatic group, such a group is preferably substituted. It may be substituted, preferably monosubstituted, suitably by an amino, or a derivative of an amino (especially a protected) group or an optionally-substituted aromatic group. Examples of protected amino groups include Fmoc- and Boc-protecting groups. A preferred aliphatic group R is of formula

I wherein X is a substituent, especially a protected amino group and $R^1$ is an optionally substituted alkyl (preferably a $C_{1-8}$, more preferably $C_{1-4}$ alkyl, especially a methyl) group.

Examples of aliphatic groups optionally-substituted by an aromatic group include a $C_{1-8}$, preferably a $C_{1-6}$, more preferably a $C_{1-4}$, especially a $C_{1-2}$, alkyl group substituted by an optionally-substituted, especially an unsubstituted, phenyl group. A preferred such group is a phenylethylyl group.

Where R represents an aromatic group, it preferably represents an optionally-substituted phenyl or optionally-substituted bicyclic (fused) group. A preferred optionally-substituted phenyl group is substituted by any of the substituents described above, the preferred ones of which include an optionally-substituted phenyl group or a nitro, alkoxy (suitably a $C_{1-8}$, preferably $C_{1-6}$, more preferably $C_{1-4}$, especially a $C_1$, alkoxy) group. A preferred bicyclic (fused) group comprises a benzo moiety fused to a five-membered heteroaromatic moiety and preferably represents a benzoheterophenyl (e.g. benzothiophenyl) group.

Preferably, group R incorporates an aromatic moiety and/or an amino group, especially a protected amino group. More preferably, group R incorporates an aromatic moiety.

Said amide may be of formula $$RCONR^2\text{-}SS \qquad \qquad II$$

wherein $R^2$ is a hydrogen atom or an optionally-substituted alkyl group and SS represents a solid support.

$R^2$ is preferably a hydrogen atom.

SS preferably includes a moiety of formula

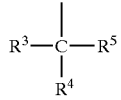

III wherein the free bond is bonded to the nitrogen atom in the amide of formula II and wherein $R^3$, $R^4$ and $R^5$, independently represent a hydrogen atom or an optionally-substituted alkyl or aromatic group, provided that at least one of groups $R^3$, $R^4$, or $R^5$ represents an optionally-substituted aromatic group. Atoms or groups on one of $R^3$ $R^4$ or $R^5$ may be bonded to another one of $R^3$ $R^4$ or $R^5$ so that bridging atoms or groups are defined between a part of one of $R^3$, $R^4$ or $R^5$ and a part of another of $R^3$, $R^4$ or $R^5$ Preferably, $R^5$ represents a hydrogen atom or an optionally-substituted, especially an unsubstituted, alkyl group. More preferably, $R^5$ represents a hydrogen atom.

Preferably, $R^3$ does not represent a hydrogen atom. Preferably, $R^3$ represents an electron-donating group. $R^3$ preferably represents an optionally-substituted aromatic group. $R^3$ may be optionally-substituted by one or more electron donating groups, for example by alkoxy, preferably $C_{1-4}$, more preferably $C_{1-2}$, especially methoxy, groups. Preferably, $R^3$ represents an optionally-substituted phenyl group. $R^3$ may be optionally-substituted by a bridging atom or group which defines a bridge between groups $R^3$ and $R^4$ Wherein $R^3$ is substituted, it is preferably substituted in the ortho- and/or para-position(s).

Preferably, $R^4$ does not represent a hydrogen atom. Preferably, $R^4$ represents an electron-donating group. $R^4$ preferably represents an optionally-substituted aromatic group. $R^4$ may be substituted by one or more electron-donating groups, for example by a group incorporating an —O— moiety. Preferably $R^4$, represents an optionally-substituted phenyl group. Where a bridge is defined between groups $R^3$ and $R^4$ said bridge may be defined by —O— or —S— moieties, especially by an —O— moiety which suitably forms with part of groups $R^3$ and $R^4$ a component of a six-membered ring. Where $R^4$ is substituted, it is preferably substituted in the ortho and/or para position(s).

Preferably, one of $R^3$ and $R^4$, more preferably $R^4$, is linked to a polymer support.

In one embodiment, SS may represent

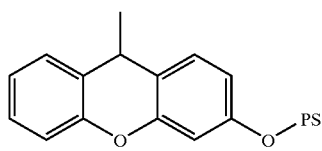

IV wherein PS represents a polymer-support and the free bond between the phenyl groups represents the point of attachment to the nitrogen atom in formula II.

In another embodiment, SS may represent

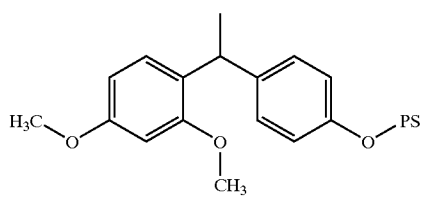

V where the free bond is as described above.

Preferably the method comprises treating said solid supported amide to cause formation of the nitrile compound and cleavage of it from the support.

Preferably, in the method, formation of the nitrile compound and cleavage of it from the support occur substantially concurrently.

Preferably, preparation of said nitrile compound involves dehydrating said solid supported amide. In the preparation of the nitrile compound, the amide may be acetylated, suitably by trifluoroacetylation, which suitably allows cleavage/dehydration in one operation. Dehydration may be undertaken in the presence of a base. Preferred dehydrating agents are highly electrophilic and may include: a nitrogen-containing base, for example an aromatic nitrogen containing base such as pyridine; an acid halide, especially an acid chloride and preferably one including an electron withdrawing group attached to the carbonyl carbon thereof, wherein suitably a haloalkyl, preferably a chloroalkyl, especially a multi-chloro alkyl, such as trichloromethyl, may be used; and Burgess reagent ((methoxycarbonylsulphamoyl) triethylammonium hydroxide inner salt).

The treatment of said solid supported amide is preferably carried out in an aprotic suitably an organic solvent. The reaction is suitably carried out at a temperature of less than 100° C., preferably less than 50° C., more preferably at less than 30° C., especially at ambient temperature.

After the treatment, the mixture produced may be filtered to separate the nitrile compound from the solid support and then isolated by standard techniques. Said solid supported amide may be prepared by treatment of an amine with a carboxylic acid or a carboxylic acid derivative. Where the nitrile compound is of formula RCN, said amine may be treated with a compound of formula

RCOY      VI wherein Y represents an hydroxy group, a carboxylic acid residue, for example a halogen atom or any electron withdrawing leaving group such as those derived from HOBt, HOAt, N-hydroxysuccinimide, 2- or 4-nitrophenol, pentafluorophenol, cyanomethyl and N, N'-dialkyl-O-acylureas.

The amine used to prepare the amide may be of general formula

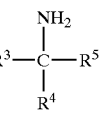

VII wherein $R^3$, $R^4$ and $R^5$ are as described above.

Preferably, the amide is prepared from the amine by contacting the amine of formula VII with said compound of formula VI, suitably in the presence of a base and suitably in an aprotic organic solvent. The reaction is preferably carried out at a temperature of less than 100° C., preferably less than 50° C., more preferably less than 30° C., especially at ambient temperature.

The invention extends to any novel nitrile compound described herein.

The invention further extends to any novel intermediate described herein.

Specific embodiments of the invention will now be described, by way of example.

Aromatic and aliphatic nitriles have been prepared through dehydration of secondary amides derived from carboxylic acids or carboxylic acid derivatives and resin bound electron rich aromatic methylamines. Schemes 1 and 2 below summarize the preparation starting from Sieber and Rink resins respectively, wherein R is an optionally-substituted aromatic or aliphatic group.

SCHEME 1

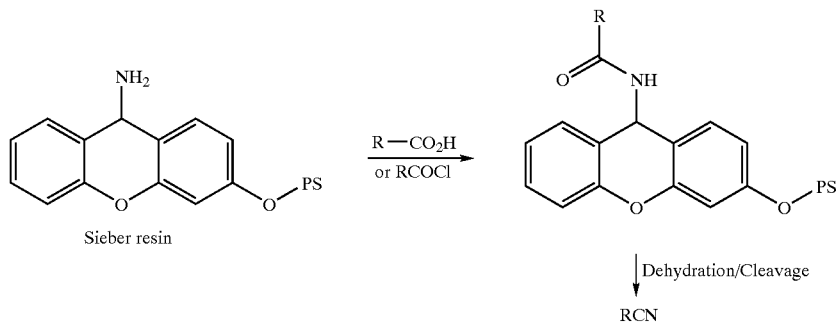

SCHEME 2

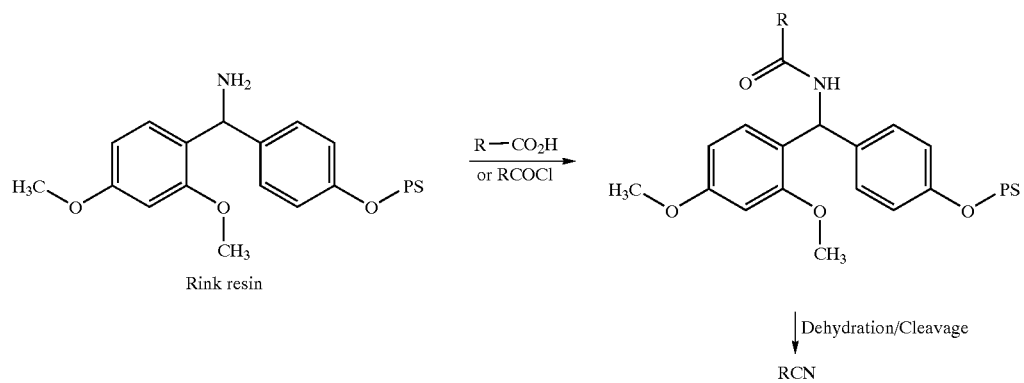

Referring to schemes 1 and 2, the Sieber and Rink resins are examples of electron rich methylamines which are reacted with carboxylic acids or acid chlorides to prepare secondary amides which can then be dehydrated, for example using excess trifluoracetic anhydride and pyridine in dry dichloromethane overnight to furnish the nitrile derivative (RCN) directly in solution.

Specific reactions undertaken are now described. Examples 1 to 10 describe the preparation of amides; and examples 11 to 24 describe the preparation of nitrile compounds from corresponding amides. In Examples 11 to 18, 23 and 24 dehydration/cleavage to the nitriles is achieved using TFAA-pyr in DCM; in examples 19 and 20, dehydration/cleavage is effected by the use of Burgess reagent; and in Examples 21 and 22 dehydration/cleavage is effected by use of trichloracetyl chloride.

The following abbreviations are used herein:
TBTU—2-(1H-benzotriazolyl)-1,1,3,3-tetramethyluronium tetrafluoroborate
HOBt—1-hydroxybenzotriazole
DIEA—N,N-diisopropylethylamine
TFAA—trifluoroacetic anhydride
DCM—dichloromethane
DMF—dimethyl formamide
Fmoc—fluorenylmethoxycarbonyl
Boc—butoxycarbonyl Resins described herein were purchased from Nova Biochem. Sieber and Rink resins were purchased in Fmoc protected forms. Deprotection, where necessary, is generally undertaken as follows: Resin (1 g) was suspended in DMF (20 ml) and piperidine (5 ml) was added. The mixture was stirred at room temperature for 30 minutes, then washed with DMF, MeOH, DCM, MeOH, DCM, MeOH and dried in vacuo.

Burgess reagent described herein may be prepared as described in G. M. Atkins, Jr and E. M. Burgess, J. Amer. Chem. Soc., 1968, 90, 4744.

EXAMPLE 1

3-Phenylpropionyl-Sieber Resin

To a suspension of Fmoc-deprotected Sieber resin (0.62 mmol/g, 150 mg) in dry DCM was added N,N-diisopropylethylamine (65 µl) followed by 3-phenylpropionyl chloride (55 µl) and the suspension stirred at ambient temperature for 2 hours. The resin was then washed (using DCM, methanol, DCM, methanol), then dried under vacuum.

EXAMPLE 2

Amide Derived From 2-Biphenyl Carboxylic Acid and Sieber Resin

To a suspension of Fmoc deprotected Sieber resin (0.62 mmol/g, 150 mg) in dry DMF was added 2-biphenyl carboxylic acid (77 mg) HOBt (29 mg), DIEA (138 µl) followed by TBTU (125 mg) and the suspension stirred at ambient temperature for 2 hours. The resin was then washed (using DMF, methanol, DCM, methanol, DCM, methanol) then dried under vacuum.

EXAMPLES 3 to 8

Following the procedure described in Example 1, amides were prepared from the Sieber resin by treatment with benzo[b]thiophen-2-carbonyl chloride (Example 3), 4-nitrobenzoyl chloride (Example 4), 2,4-dimethoxybenzoyl chloride (Example 5), Fmoc-L-alanine (Example 6), Boc-L-alanine (Example 7) and 1,2,3,4-tetrahydronaphthoic acid (Example 8).

EXAMPLE 9

3-Phenylpropionyl-Rink Resin

To a suspension of Fmoc deprotected Rink resin (0.59 mmol/g, 220 mg) in dry DCM was added DIEA (112 μl) and 3-phenylpropionyl chloride (96 μl) and the mixture stirred at ambient temperature for 1 hour. The resin was then washed using DCM, methanol, DCM, methanol, then dried under vacuum.

EXAMPLE 10

Amide Derived From 4-Biphenylcarbonyl Chloride and Rink Resin

To a suspension of Fmoc deprotected Rink resin (0.59 mmol/g, 220 mg) in dry DCM was added DIEA (112 μl) and 4-biphenylcarbonyl chloride (140 mg) and the mixture stirred at ambient temperature for 1 hour. The resin was then washed using DCM, methanol, DCM, methanol, then dried under vacuum.

EXAMPLE 11

3-Phenylpropionitrile

A solution of trifluoroacetic anhydride (43 μl) and dry pyridine (50 μl) in dry DCM (1.5 ml) was added to the resin prepared in example 1 (0.62 mmol/g, 100 mg) and the suspension stirred under nitrogen at ambient temperature overnight. The cleavage solution was filtered from the resin and evaporated to dryness. The residue was redissolved in ethyl acetate, washed with saturated $NaHCO_{3(aq)}$, 1M $KHSO_4$, dried ($MgSO_4$) and evaporated to yield 3-phenylpropionitrile (8 mg, 98%).

$v_{max}$ 2249 cm$^{-1}$; $\delta_H$ 2.55 (2 H, t), 2.91 (2 H, t), 7.2 (5 H, m).

EXAMPLE 12

Benzo[b]thiophene-2-carbonitrile

The resin prepared in Example 3 (0.62 mmol/g, 100 mg) was treated as described in Example 11 to give benzo[b]thiophene-2-carbonitrile (5 mg, 51%).

$v_{max}$ 2213 cm$^{-1}$; $\delta_H$ 7.45 (2 H, m), 7.83 (3 H, m).

EXAMPLE 13

4-Nitrobenzonitrile

The resin prepared in Example 4 (0.62 mmol/g, 100 mg) was treated as described in Example 11 to give 4-nitrobenzonitrile (9 mg, 98%)

$v_{max}$ 2232 cm$^{-1}$; $\delta_H$ 7.84 (2 H, d), 8.30 (2 H, d).

EXAMPLE 14

2,4-Dimethoxybenzonitrile

The resin prepared in Example 5 (0.62 mmol/g, 100 mg) was treated as described in Example 11 to give 2,4-dimethoxybenzonitrile (6 mg, 60%).

$v_{max}$ 2217 cm$^{-1}$; $\delta_H$ 3.79 (3 H, s), 3.84 (3 H, s), 6.4 (1 H, s), 6.45 (1 H, d) 7.41 (1 H, d) m/z (ES+) 164 (M+H).

EXAMPLE 15

Biphenyl-2-carbonitrile

The resin prepared in Example 2 (0.62 mmol/g, 100 mg) was treated as described in Example 11 to give 2-biphenylcarbonitrile (9 mg, 82%).

$v_{max}$ 2222 cm$^{-1}$; $\delta_H$ 7.44 (7 H, m), 7.58 (1, H, t), 7.7 (1, H, d).

EXAMPLE 16

2-(Fmoc-amino)-2-methylacetonitrile

The resin prepared in Example 6 (0.62 mmol/g, 100 mg) was treated as described in Example 11 to give 2-(Fmoc-amino)-2-methylacetonitrile (9 mg, 50%).

$\delta_H$ 1.49 (3 H, d), 4.16 (1 H, m), 4.43 (2 H, d), 4.62 (1 H, m), 4.99 (1 H, m), 7.26 (2 H, t), 7.35 (2 H, t), 7.50 (2 H, d), 7.70 (2, H, d). m/z (ES+) 293 (M+H).

EXAMPLE 17

2-(Boc-amino)-2-methylacetonitrile

The resin prepared in Example 7 (0.62 mmol/g, 100 mg) was treated as described in Example 11 to give 2-(Boc-amino)-2-methylacetonitrile (9 mg, 86%).

$\delta_H$ 1.41 (9 H, s), 1.49 (3 H, d), 4.55 (1 H, m), 4.75 (1 H, m); m/z (ES+) 171 (M+H).

EXAMPLE 18

1,2,3,4-Tetrahydro-2-naphthocarbonitrile

The resin prepared in Example 8 (0.62 mmol/g, 100 mg) was treated as described in Example 11 to give 1,2,3,4-tetrahydro-2-naphthocarbonitrile (9 mg, 93%).

$v_{max}$ 2237 cm$^{-1}$; $\delta_H$ 2.02 (1 H, m), 2.15 (1 H, m), 2.79 (1 H, m), 2.89–3.11 (4 H, m) 6.95–7.16 (4 H, m).

EXAMPLE 19

Biphenyl-2-carbonitrile

The resin prepared in Example 2 (0.62 mmol/g, 100 mg) suspended in dry THF was treated with (methoxycarbonylsulphamoyl)triethylammonium hydroxide, inner salt (Burgess reagent) (44 mg) and the mixture refluxed under nitrogen overnight. The cleavage solution was filtered from the resin and evaporated to dryness. The residue was redissolved in ethyl acetate, washed with water, dried ($MgSO_4$) and evaporated to yield biphenyl-2-carbonitrile (2 mg, 18%).

$v_{max}$ 2222 cm$^{-1}$; $\delta_H$ 7.44 (7 H, m), 7.58 (1 H, t), 7.7 (1 H, d).

EXAMPLE 20

3-Phenylpropionitrile

The resin prepared in Example 1 (0.62 mmol/g 100 mg) was treated as described in Example 19 to give 3-phenylpropionitrile (7 mg, 86%).

$v_{max}$ 2249 m$^{-1}$; $\delta_H$ 2.55 (2 H, t), 2.91 (2 H, t), 7.2 (5 H, m).

EXAMPLE 21

Biphenyl-2-carbonitrile

The resin prepared in Example 2 (0.62 mmol/g, 100 mg) suspended in dry DCM was treated with triethylamine (47

μl) and trichloroacetyl chloride (34 μl) and the mixture stirred at ambient temperature under nitrogen overnight. The cleavage solution was filtered from the resin and evaporated to dryness. The residue was redissolved in ethyl acetate, washed with saturated $NaHCO_3$(aq), 1M $KHSO_4$, dried ($MgSO_4$) and evaporated. The residue was chromatographed on silica gel using ethyl acetate/hexane (1:9) for elution, yielding biphenyl-2-carbonitrile (7 mg, 64%).

$v_{max}$ 2222 $cm^{-1}$; $δ_H$ 7.44 (7 H, m), 7.58 (1 H, t), 7.7 (1 H, d).

EXAMPLE 22

3-Phenylpropionitrile

The resin prepared in Example 1 (0.62 mmol/g, 100 mg) was treated as described in Example 20 to give 3-phenylpropionitrile (6 mg, 74%)

$v_{max}$ 2249 $cm^{-1}$; $δ_H$ 2.55 (2 H, t), 2,91 (2 H, t), 7.2 (5 H, m).

EXAMPLE 23

3-Phenylpropionitrile

A solution of trifluoroacetic anhydride (83 μl) and dry pyridine (91 μl) in dry DCM (3 ml) was added to the resin prepared in Example 11 (0.59 mmol/g,200 mg) and the suspension stirred under nitrogen at ambient temperature overnight. The cleavage solution was filtered from the resin and evaporated to dryness. The residue was redissolved in ethyl acetate, washed with saturated $NaHCO_3$(aq), 1M $KHSO_4$, dried ($MgSO_4$) and evaporated to yield 3-phenylpropionitrile (15 mg, 100%).

$v_{max}$ 2249 $cm^{-1}$; $δ_H$ 2.55 (2 H, t), 2.91 (2 H, t), 7.2 (5 H, m).

EXAMPLE 24

4-Biphenylcarbonitrile

A solution of trifluoroacetic anhydride (83 μl) and dry pyridine (91 μl) in dry DCM (3 ml) was added to the resin prepared in Example 10 (0.59 mmol/g, 200 mg) and the suspension stirred under nitrogen at ambient temperature overnight. The cleavage solution was filtered from the resin and evaporated to dryness. The residue was redissolved in ethyl acetate, washed with saturated $NaHCO_3$(aq), 1M $KHSO_4$, dried ($MgSO_4$) and evaporated to yield 4-biphenylcarbonitrile (22 mg, 100%).

$δ_H$ 7.30–7.70 (9 H, m).

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extend to any novel one, or any novel combination, of the features disclosed in this specification (including any accompanying claims, abstract and drawings), or to any novel one, or any novel combination, of the steps of any method or process so disclosed.

What is claimed is:

1. A method of preparing a nitrile compound, the method comprising treating a solid supported amide to cause formation of the nitrile compound and cleavage from the support.

2. A method according to claim 1, wherein said amide is treated to dehydrate it.

3. A method according to claim 2, wherein cleavage and dehydration of the amide are accomplished in one operation.

4. A method according to claim 1, wherein said nitrile compound is of formula RCN where R represents an optionally-substituted alicyclic, aliphatic or aromatic (which includes heteroaromatic) group.

5. A method according to claim 4, wherein group R incorporates an aromatic moiety and/or an amino group.

6. A method according to claim 1, wherein said amide is of formula $RCONR^2$-SS wherein $R^2$ is a hydrogen atom or an optionally-substituted alkyl group and SS represents a solid support.

7. A method according to claim 6, wherein SS includes a moiety of formula

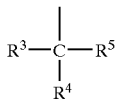

wherein the free bond is bonded to the nitrogen atom in the amide of formula II and wherein $R^3$, $R^4$ and $R^5$, independently represent a hydrogen atom or an optionally-substituted alkyl or aromatic group, provided that at least one of groups $R^3$, $R^4$, or $R^5$ represents an optionally-substituted aromatic group.

8. A method according to claim 6, wherein $R^5$ represents a hydrogen atom.

9. A method according to claim 6, wherein $R^3$ represents an optionally-substituted aromatic group.

10. A method according to claim 7, wherein $R^4$ represents an optionally-substituted aromatic group.

11. A method according to claim 7, wherein one of $R^3$ or $R^4$ is linked to a polymer support.

12. A method according to claim 1, wherein formation of the nitrile compound and cleavage of it from the support occur substantially concurrently.

13. A method according to claim 1, wherein, in the method, the amide is acetylated.

14. A method according to claim 1, wherein said solid supported amide is treated in the presence of a base.

15. A method according to claim 1, wherein said solid supported amide is treated in an aprotic solvent.

16. A method according to claim 1, wherein said solid supported amide is treated at a temperature not exceeding 100° C. to prepare said nitrile compound.

17. A method according to claim 1, wherein the nitrile compound is separated from the support by filtration.

18. A method of preparing a nitrile compound, the method comprising treating a solid supported amide to cause formation of the nitrile compound and cleavage from the support, wherein said amide is of formula $RCONR^2$-SS, wherein R represents an optionally-substituted alicyclic, aliphatic or aromatic group, $R^2$ is a hydrogen atom or an optionally-substituted alkyl group and SS represents a solid support.

19. A method of preparing a nitrile compound, the method comprising treating a solid supported amide to cause formation of the nitrile compound and cleavage from the support, wherein formation of the nitrile compound and cleavage of it from the support occur substantially concurrently.

20. An intermediate amide compound of formula $RCONR^2$-SS, wherein R represents an optionally substituted alicyclic, aliphatic or aromatic group, $R^2$ is a hydrogen atom or an optionally-substituted alkyl group and SS represents a solid support.

* * * * *